(12) United States Patent
Lomanto et al.

(10) Patent No.: US 6,205,355 B1
(45) Date of Patent: Mar. 20, 2001

(54) ELECTROCARDIOGRAPH LEADWIRE ASSEMBLY

(76) Inventors: Marisa Lomanto, 2914 W. Stony Hill Ct., #3A, Richmond, VA (US) 23235; William Doherty Motherway, 548 Orange St., #202, New Haven, CT (US) 06510

(\*) Notice: Subject to any disclaimer, the term of this patent is extended or adjusted under 35 U.S.C. 154(b) by 0 days.

(21) Appl. No.: 09/250,140

(22) Filed: Feb. 16, 1999

(51) Int. Cl.⁷ .................................................. A61B 5/0402
(52) U.S. Cl. ........................................................... 600/509
(58) Field of Search .................................. 600/508, 509, 600/512, 523, 524, 525, 544, 393, 372; 607/75, 115

(56) References Cited

U.S. PATENT DOCUMENTS

| | | |
|---|---|---|
| 2,650,990 * | 9/1953 | Woodruff ................................ 607/75 |
| 3,960,141 | 6/1976 | Bolduc . |
| 4,249,538 | 2/1981 | Musha et al. . |
| 4,419,998 | 12/1983 | Heath . |
| 4,715,382 | 12/1987 | Strand . |
| 5,033,474 * | 7/1991 | Varelis et al. ......................... 600/509 |
| 5,042,498 | 8/1991 | Dukes . |
| 5,307,818 | 5/1994 | Segalowitz . |
| 5,813,979 * | 9/1998 | Wolfer ................................. 600/508 |

\* cited by examiner

Primary Examiner—William E. Kamm
(74) Attorney, Agent, or Firm—Malloy & Malloy, P.A.

(57) ABSTRACT

An electrocardiograph leadwire assembly to be used with a plurality of electrodes, from which it receives cardiac electrical signals, and with an electrocardiograph monitoring unit, to which it transmits the electrical signals for processing and eventual display of the electrocardiogram. The leadwire assembly includes a plurality of leadwires connected in electrical communication between a different one of the electrodes and an associated port on the electrocardiograph monitoring unit, and a main housing wherein at least one of the leadwires is selectively retracted into an individual, isolated, retracted position within the main housing such that all of the leadwires are maintained untangled and prepared for immediate extension from the main housing for use when needed.

27 Claims, 7 Drawing Sheets

ELECTROCARDIOGRAPH LEADWIRE ASSEMBLY

BACKGROUND OF THE INVENTION

1. Field of the Invention

The invention relates generally to an electrocardiograph leadwire assembly, and more specifically to an electrocardiograph leadwire assembly which enables convenient and safe implementation of a variety of leadwire number and positioning configurations in a durable, quickly accessible and adaptable, compact, easily storable, and safe assembly.

2. Background of the Invention

A heart beats as the result of electrical activity occurring within its individual cells. These small electric forces are conducted throughout the body and can be measured at the body's surface and studied. Electrocardiography, the study of these cardiac electrical signals, provides the clinician with valuable information on a patient's cardiac status. It can allow for the early detection, and thus treatment, of such cardiac disorders as dysrhythmias, conduction abnormalities, myocardial ischemia/infarction, and adverse drug and electrolyte effects.

An electrocardiograph is an instrument that detects the cardiac electrical activity at the body's surface, then processes and displays this information to produce a visible record. The device continuously monitors the voltage differences between at least two body surface electrodes over time, and records them to create a curve called an electrocardiogram (ECG). The ECG is thus a continuous voltage-time record which can provide essentially "real-time" information about cardiac electrical activity.

More specifically, the voltage differences are detected by means of a number of conductive electrodes placed on the body surface. Each of the electrodes is connected to the electrocardiograph unit by a leadwire. A continuously varying difference in voltage between at least two electrodes is measured and displayed. This continuously varying voltage difference between at least two electrodes, occupying at least two different positions in the heart's electric field is called a "lead". This is in contradistinction to a "leadwire", which is the wire that actually carries the electric current. A lead therefore will assume different configurations depending upon the location of the electrodes being evaluated.

The monitored cardiac electrical activity can be presented in several forms. Most electrocardiographs will display the ECG in "real-time" on a video display-monitor, as well as record a tracing of the curve on graded strip paper. Generally, the device will display one to three ECG leads simultaneously on the video-display monitor, with the video-display lead(s) chosen by means of a channel select.

There are three primary ECG configurations in clinical use today. These configurations allow the monitoring of from 1 to 12 leads and require either 3, 5, or 10 leadwires, connected with the electrocardiograph unit and extending to the patient. The most complete type of ECG monitors 12 leads, from 10 electrodes placed at 10 standard locations on the patient's body, and thus produces 12 different voltage-time graphs. Some leads are more "sensitive" than others in detecting certain abnormalities, with different leads and lead combinations providing better "views" of different aspects of the heart's electrical activity. Furthermore, sensitivity and diagnostic capability are generally increased by monitoring more than one lead, such that the combination of multiple leads provides a more complete picture of the heart's activities. However, because different clinical situations require different types and amounts of information, a clinician may generally wish to tailor the number and configuration of leads being employed to the particular application.

The conventional, non-retractable ECG wires commonly used today have certain problems and limitations. For example, ECG leadwires, due to their length and current design, create a storage problem when not in use. As a result, clinicians often struggle to find out-of-the-way locations in which to maintain the wires. Unfortunately, however, the leadwire assembly is often hung from intravenous ("IV") poles, the ECG monitoring unit or various other medical equipment, or is curled into a bundle and rested on a flat surface. When stored in this manner, the leadwires are easily displaced and/or tangled, take up much space, and are susceptible to damage. Furthermore, it can be hazardous to have long wires strewn about an often crowded monitoring environment, such as an operating room ("O.R.") or ambulance.

Tangling of leadwires is an extremely common problem. All the leadwires, and particularly the longer limb leadwires, tend to become easily tangled among themselves and other objects. Accordingly, when these wires need to be used, a clinician must frequently struggle to untangle them. This is not only frustrating and time-consuming, but potentially dangerous when immediate monitoring is needed or the clinician's time and attention should be directed elsewhere.

Another important problem associated with electrocardiograph leadwires and their manner of storage relates to damage. Hospitals, in particular, contain a great deal of heavy equipment, much of it mobile and in confined areas where people quickly move around. The electrocardiograph unit itself is often mobile. If the leadwires are carelessly positioned they can become kinked, entangled with and/or run over by people and heavy equipment. The type of damage that results is often difficult to detect and can arise over time. Accordingly, untimely malfunctions and/or unreliable ECG signals can result when the electrocardiograph is being relied on to provide accurate and critical cardiac monitoring.

In addition, clinical situations change quickly and unexpectedly. A clinician often cannot anticipate which particular ECG configuration will be required until a specific medical circumstance arises and the needs of the patient can be assessed. Therefore a situation can arise in which a clinician, after having already begun a procedure or treatment using a "three-lead" monitoring configuration, wishes to monitor additional leads because of an unanticipated development. It is time consuming and often not feasible to change to another device containing more leadwires. The clinician's diagnostic capability is therefore limited by the inflexibility of the present ECG device.

Thus, there is a substantial need in the art relating to electrocardiographs to provide an electrocardiograph leadwire assembly which allows its leadwires to be protected and stored out of the way when not in use. Such a device would increase the life and long-term accuracy of the electrocardiograph and would also eliminate a source of hazard often present in most monitoring environments. Furthermore, there is a need for an electrocardiograph leadwire assembly which will not require a substantial amount of a clinician's time and attention to untangle, locate, or otherwise implement. There is also a need for an electrocardiograph leadwire assembly which will allow for a varying number of leadwires to be used, so as to accommodate a variety of monitoring configurations, while leaving the remaining leadwires protected.

SUMMARY OF THE INVENTION

The present Invention fulfills the need in the art. Broadly described, the present invention relates to an improved electrocardiograph leadwire assembly that relays cardiac electrical impulses from an electrode on a patient's skin to an electrocardiograph monitoring device.

The present invention is structured to be implemented with a standard electrocardiograph monitoring unit and a plurality of electrodes. Generally, each of the electrodes are structured for conductive engagement with a patient's skin, and accordingly, they will receive the electrical signal from the patient's heart. The electrocardiograph monitoring unit is of a conventional type and includes receiving means, processing means and display means. The electrical signals detected by each of the electrodes, and relayed through the respective leadwire, are received by the receiving means of the electrocardiograph monitoring unit and are appropriately processed (e.g. amplified and filtered) to produce electrocardiograph lead signals. The electrocardiograph lead signals are then visually displayed on the display means of the electrocardiograph monitoring unit to produce the electrocardiogram.

Specifically, the electrocardiograph leadwire assembly of the present invention is structured to be disposed in connecting, preferably electrical, information transmitting communication between the plurality of electrodes and the electrocardiograph monitoring unit. Included in the electrocardiograph leadwire assembly are a plurality of leadwires. Each of the leadwires is connected in preferably electrical, information transmitting communication between a different one of the electrodes and an associated port on the electrocardiograph monitoring unit. As such, the leadwires provide for the accurate transmission of the cardiac electrical signals received by each of the electrodes to the electrocardiograph monitoring unit.

The electrocardiograph leadwire assembly further includes a main housing. The main housing is structured and disposed to contain at least one of the leadwires in individual, isolated, retracted relation therein. Further, the main housing includes retraction means therein. The retraction means are structured and disposed to selectively retract at least one leadwire into the main housing such that the portion of the leadwire exposed from the main housing can be individually controlled and its movement accordingly limited. Additionally, the retraction means retracts the leadwire into the main housing such that the leadwire is maintained untangled and prepared for extension from the main housing when use of the device is required.

Accordingly, it is an object of the present invention to provide an improved electrocardiograph leadwire assembly which, as a result of the retractable nature of each leadwire, will have a substantially extended life and be safe to use.

It is a further object of the present invention to provide an electrocardiograph leadwire assembly which is substantially compact.

Another object of the present invention is to provide an electrocardiograph leadwire assembly whose leadwires will remain securely and unobtrusively stored when not in use, so as to minimize their risk of damage and entanglement with themselves and other devices.

An additional object of the present invention is to provide an electrocardiograph leadwire assembly whose leadwires are not susceptible to entanglement that would require difficult and time consuming untangling prior to implementation thereof.

A further object of the present invention is to provide an electrocardiograph leadwire assembly which is easily and efficiently adapted for use in various clinical situations wherein varied numbers and configurations of leadwires are utilized.

These and other objects, features, and advantages of the present invention may be more clearly understood and appreciated from a review of the following detailed description of the disclosed embodiment and by reference to the appended drawings and claims.

BRIEF DESCRIPTION OF THE DRAWINGS

For a fuller understanding of the nature of the present invention, reference should be made to the following detailed description taken in connection with the accompanying drawings in which.

Like reference numerals refer to like parts throughout the several views of the drawings.

DETAILED DESCRIPTION

Referring now to the figures, the present invention is directed towards an improved electrocardiograph leadwire assembly, generally indicated as 70. The electrocardiograph leadwire assembly 70 is structured for implementation in an operating room, intensive care unit, emergency room, clinician's office, ambulance or other medical environment where a patient's heart must be monitored.

Specifically, the electrocardiograph leadwire assembly 70 is structured to be connected in information transmitting communication, such as electrical communication, with a number of electrodes 15, in a manner to be described subsequently. The electrodes 15 include conductive contacts structured to be affixed to a patient's skin, so as to receive and conduct the electrical signal emitted by the patient's heart. As can be appreciated there are a variety of different electrodes and attachment methods currently employed in the art relating to ECG devices. Any of such methods which effectively secure the electrode to the patient's body and accurately receive and conduct the electrical signals can be effectively employed within the scope of the present invention.

Connected with the plurality of electrodes 15 by the electrocardiograph leadwire assembly 70 is a standard electrocardiograph monitoring unit 30. The electrocardiograph monitoring unit 30, which can be of a number of conventionally known and accepted configurations and designs, preferably includes receiving means. The receiving means are associated with the individual electrodes 15 and their respective leadwires 100, preferably through a number of associated ports at an input jack 35 thereof, which is located on the electrocardiograph monitoring unit 30 and preferably includes a pin connector type configuration 800, as best seen in FIG. 1A. The receiving means are structured to receive the cardiac electrical signals detected and/or received by the electrodes 15 and transmitted by the electrocardiograph leadwire assembly 70. Additionally, the electrocardiograph monitoring unit 30 includes processing means contained therein. The processing means may be of any conventional type structured to process, such as by amplifying and filtering, the electrical signals received by the receiving means, to thereby produce electrocardiograph lead signals. These electrocardiograph lead signals are then displayed on the electrocardiograph monitoring unit 30 by display means, such as an analog visual display 40, and/or a printed strip 40'. Further, it is preferred that the electrocardiograph monitoring unit 30 be capable of selecting and displaying multiple varied lead signals.

Disposed in connecting relation between the input jack 35 of the receiving means of the electrocardiograph monitoring unit 30 and the electrodes 15 is the electrocardiograph leadwire assembly 70. Preferably, the leadwire assembly 70 is structured to contain a number of retractable leadwire units, identified for clarity as retractor units 80, and a corresponding number of leadwires 100; however, for clarity, and as illustrated in FIGS. 1–3, 4A, & 4B, a single retractor unit 80 configuration of the electrocardiograph leadwire assembly 70 is disclosed. An actual assembly could employ any number of retractor units 80 depending upon the number of leadwires 100 contained. Later, with respect to FIGS. 4, 5, 5A and 5B, various arrangements of multiple retractor units 80 shall be discussed.

The electrocardiograph leadwire assembly 70, generally, includes a plurality of leadwires 100. Each of these leadwires 100 is structured to be connected in information transmitting communication between a different one of the electrodes 15 and its associated port at the input jack 35 of the receiving means, so as to provide for the accurate transmission of the electrical signals received by each of the electrodes 15.

Additionally, the electrocardiograph leadwire assembly 70 includes a main housing 300. The main housing 300, which is preferably somewhat compact, is structured to contain at least one, but preferably all of the leadwires 100 in individual, isolated, retracting relation therein such that they will not become tangled with one another or any external article when not in use. Included in the main housing 300 are retraction means. The retraction means are structured and disposed to selectively retract at least one corresponding leadwire 100 into the main housing 300 such that the length of the portion of the leadwire 100 that remains exposed from the housing 300 can be individually controlled. Further, the retraction means functions to ensure that the leadwire 100 is maintained untangled and prepared for extension from the main housing 300 when not in use. Accordingly, it can be seen that the retraction means, either individually or in combination with the main housing 300 makes up the individual retractor unit(s) 80 of the leadwire assembly 70.

An individual retractor unit 80 of the electrocardiograph leadwire assembly 70, as illustrated in FIGS. 1–3 & 4A, includes a stationary shaft 400, preferably affixed to the main housing 300, on which each retractor unit 80 rotates. More particularly the retractor unit 80 may include a reel 500 disposed in rotating orientation about the shaft 400. As will be explained in greater detail hereafter, in order to allow independent retractability of multiple leadwires 100, a separate reel 500 is preferably provided for each leadwire 100. Each reel 500 preferably includes a pair of circular flanges 520 and a circumferential annulus (or drum) 540. The drum 540 is disposed about the shaft 400 such that the drum 540, and accordingly the entire reel 500, rotate freely about the shaft 400.

The retractor unit 80 also includes, at least as part of the leadwire 100, an anterior leadwire 100'. The anterior leadwire 100' is preferably made up of insulation 110 surrounding at least one, but can accommodate a pair of individually insulated interior wires 112 and 114. It is noted, however, that depending upon the ultimate function of the leadwire 100, insulation may or may not be necessary. As such, in the preferred embodiments from one to three insulated leadwires 100 may be provided for conductive functioning. The anterior leadwire 100' is structured to wrap around the drum 540 so as to be wound in an ordered, easy to unwind, retracted orientation. Further, the flanges 520 of the reel 500 function to contain the anterior leadwire 100' about the drum 540 during retraction and extension.

Figure 1:
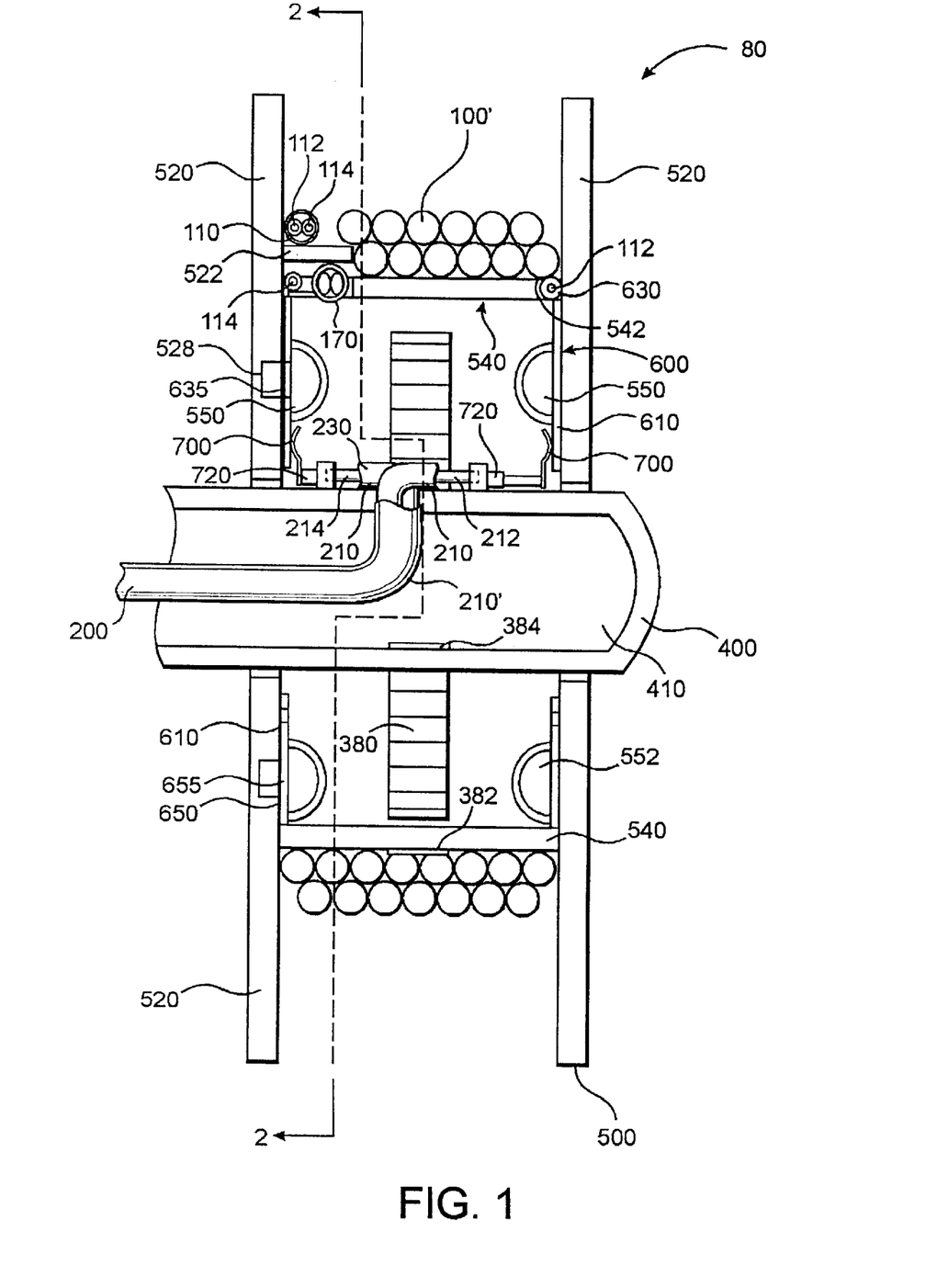
FIG. 1 is a longitudinal section of a first embodiment of one retractor unit of the leadwire assembly of the present invention.
Figure 1A:
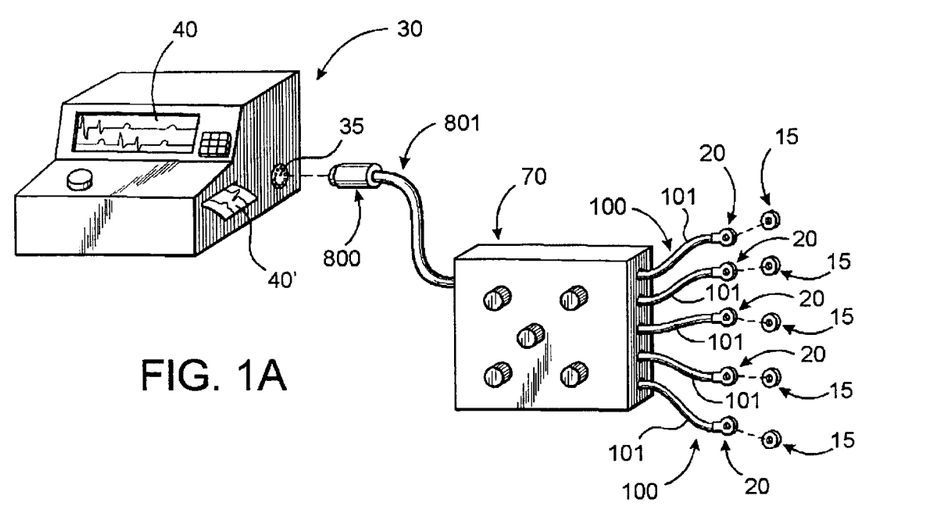
FIG. 1A is an isometric view of one embodiment of the present invention.

The anterior leadwire 100' of each of the leadwires 100 includes a distal end 101, as in FIGS. 1 and 1A, and a proximal end 170. Preferably, the electrode 15 (not shown in FIG. 1 for clarity), placed on the patient's skin, is secured at the distal end 101 of the anterior leadwire 100' by an electrode connector 20, as in FIG. 1A. It is noted that the electrode connector 20 can be of any number of configurations, such as a clip or preferably a snap connector which permits secure connection of the anterior leadwire 100' with a preferably disposable electrode 15. The anterior leadwire 100' is preferably five to six feet in length for limb (PA, LA, RL, LL) leads and at least two feet in length for precordial ($V_1$–$V_6$) leads. At the proximal end 170 of the anterior leadwire 100', the anterior leadwire 100' is split into its component wires 112, 114, and each is conductively affixed to an anterior contact 600. It is noted that in an alternative embodiment wherein the anterior leadwire 100' includes only a single component wire, only one anterior contact 600, as illustrated in FIG. 4A, need be included, and the conductive assembly to be described subsequently is accordingly adapted to accommodate the single wire by eliminating extraneous and duplicate components.

Figure 6A:
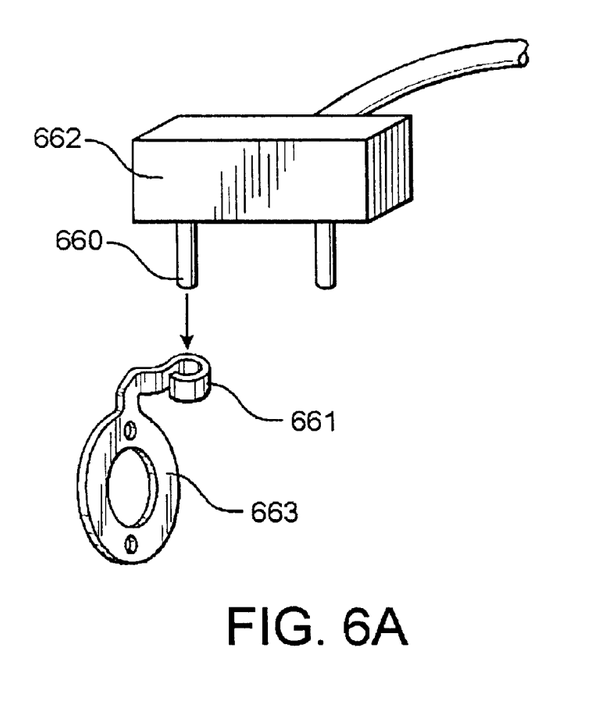
FIG. 6A is an isometric view of a pin and socket connector.
Figure 6B:
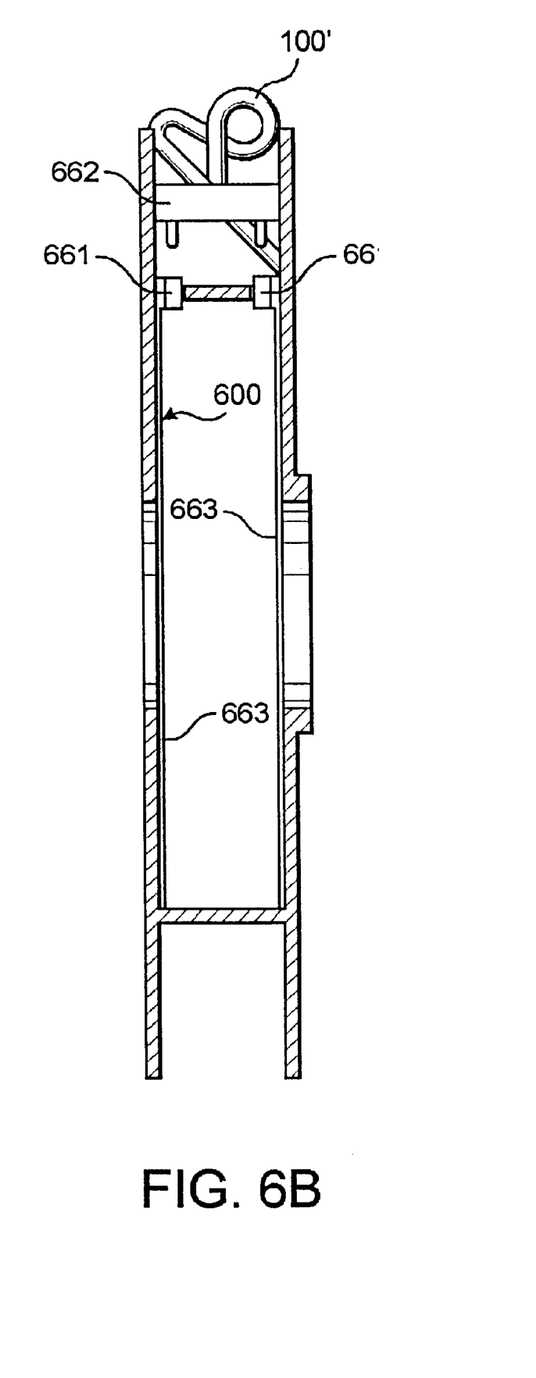
FIG. 6B is a longitudinal section of the pin and socket connector of FIG. 6A.

Each of the anterior contacts 600, which are conductive elements preferably formed of copper or a like conductive material, is affixed to the reel 500 and therefore rotates with the reel 500. In a first embodiment, seen in FIG. 1, each anterior contact 600 includes primarily a ring 610 which is located at the interior of the drum 540 of the reel 500 and is affixed to the inside of the flange 520, so that the two anterior contacts 600 face one another inside the reel 500. Preferably, however, the contact with the anterior leadwire 100' occurs outside the drum 540. This is accomplished by a contact appendage 630 which extends through aperture 542 in the drum 540. There, the stripped, non-insulated ends of the component wires 112, 114 are each connected to the corresponding contact appendage 630 by any suitable means, such as crimp connection or soldering. Additionally, the anterior contact 600 includes an anchor appendage 650 extending in opposite direction to the contact appendage 630. This anchor appendage 650 functions to provide a more secure engagement between the anterior contact 600 and the reel 500 and to provide more stability upon rotation of the reel and hence, the anterior contact 600 about the shaft 400. Preferably, plastic fasteners 550 are bonded to the reel 500 through openings 635, 655 in the contact and anchor appendages 630, 650. Accordingly, the heads 552 of fasteners 550 serve two purposes, namely to hold the anterior contacts 600 in place and also to provide a buffer for biasing means 380, which is preferably disposed about the shaft 400 between the anterior contacts 600 and thus might produce a short between the contacts 600 if not buffered. Alternatively, however, as illustrated in FIGS. 6A and 6B, instead of a crimp or soldered connection, a pin 660 and socket 661 connector may be utilized to connect the non-insulated ends of component wires 112 and 114 to the corresponding anterior contacts 600. Such a pin 660 and socket 661 connector allows for the replacement of individual anterior leadwires, in case of damage. As seen in the figures, the anterior leadwire 100' terminates in a hub 662 from which one or more conductive pins 660 extend into coupled engagement with the conductive socket 661. The conductive socket 661 of this embodiment is preferably formed with a ring contact 663 incorporated with the anterior contacts 600 with appropriate modifications to the housing so as to permit facilitated removal of the anterior leadwire 100', hub 662 and pin 660 complex from the socket 661 for replacement.

Specifically, the biasing means 380, is preferably a constant force spring 380. The spring 380 is structured to bias the reel 500 in a direction which will cause the anterior leadwire 100' to wind about the drum into a retracted orientation. It is preferred that a clock-type spring be used, as it should allow several rotations (more than 20 rotations may be needed) of the reel 500 without considerable increase in leadwire tension. Further, any suitable material, such as stainless or spring steel may be used, but BeCu provides a lower modulus of elasticity, allowing a tighter bend radius at some expense of spring force. Although many different types of springs may be utilized, the brand-name "Spirator"™ spring is particularly suited for this application. In use, the inner tang 384 of the spring 380 is affixed to the shaft 400 and the outer tang 382 is affixed to the drum 540. Accordingly, when the anterior leadwire 100' is unwound from about the drum 540 of the reel 500 into an extended orientation, the reel 500 rotates in a first direction and the spring 380 is tensed. When, however, affirmative retention of the anterior leadwire 100' in the extended orientation is terminated, the natural recoil of the spring 380 rotates the reel 500 in a second, opposite direction relative to the shaft 400 until the anterior leadwire 100' is wound into its retracted orientation.

The individual retractor unit 80 of the first embodiment of the leadwire assembly 70 further includes a pair of medial contacts 700. Of course, in the case of an anterior leadwire 100' including only one component wire, only one medial contact is needed, as in FIG. 4A. The medial contacts 700 are affixed to the shaft 400 by molding into medial leadwire anchors 720, which are preferably of plastic or another non-conductive material. Each medial contact 700 is lightly biased against the ring 610 of its respective anterior contact 600. The biasing should not be so forceful as to promote galling or sticking as the anterior contact 600 rotates. Rather, the biasing should be sufficient to ensure that the medial contact 700 maintains its contact with anterior contact 600 even as the reel rotates. It is seen that the continuous contact between the anterior and medial contacts 600, 700 could be accomplished by a slip-ring method in an alternate embodiment, so long as the connection provides minimal conductive resistance.

Also preferably included in the first embodiment of the assembly of the present invention is a medial leadwire 200. The medial leadwire 200 is made up of a pair of preferably individually insulated wires 212, 214, in the case of an anterior leadwire 100' with two component wires, which may be surrounded by individual insulation 210 and common insulation 210'. At its distal end 230, the medial leadwire 200 is split into its complementary pair of wires 212, 214. Each wire 212, 214 is connected, such as by crimp connection or soldering, to its respective medial contact 700. Further, these connections can be sunken in the leadwire anchors 720 to reduce the chances of shorting by the spring 380. In the case of an anterior leadwire 100' containing only one component wire and making only one contact, the medial leadwire need contain only one insulated component wire, as in FIG. 4A. The medial leadwire 200 is structured to pass through an aperture into the hollow bore 410 of the shaft 400 so as to connect at its proximal end to the ECG monitoring unit. The medial leadwire 200 does not necessarily have to pass through the shaft 400, but this simplifies operation, particularly when multiple reels 500 are employed. Upon exiting the shaft 400 the one or more preferably individually insulated medial leadwires 200, each corresponding to a respective anterior leadwire 100', preferably travel together within an insulated ECG common cable 801 and terminate at an ECG monitoring unit connector 800, which "plugs in" or is otherwise matingly connected with a corresponding ECG input jack 35 on the ECG monitoring unit.

In summary, the cardiac electrical signal is detected first at the patients' skin, is conducted via an electrode 15, through the electrode connector 20 to the anterior leadwire 100', which itself can be extended by unwinding it from reel 500. The anterior leadwire 100' carries the electrical signal, via a contact appendage 630, or the aforementioned pin 660 and socket 661 connector, to the anterior contact 600 which is affixed to and rotates with the reel 500. The anterior contact 600, in turn, conducts the signal to the medial contact 700, which remains stationary and fixed to the shaft 400. The medial leadwire 200 conducts the signal from the medial contact 700 through the shaft 400 and common cable 801, through which it travels, to the electrocardiograph monitoring unit. Depending upon the components and equipment used, an amplifier, either near the electrical source, such as the electrode, or within the monitoring unit itself, may be included to enhance the electrical signal. Further, the electrical signal may include shielded, filtered, reference signals, and the electrical resistances may be modified in order to optimize performance. These adjustment factors, however, are matters within the scope of the known art.

Figure 4:
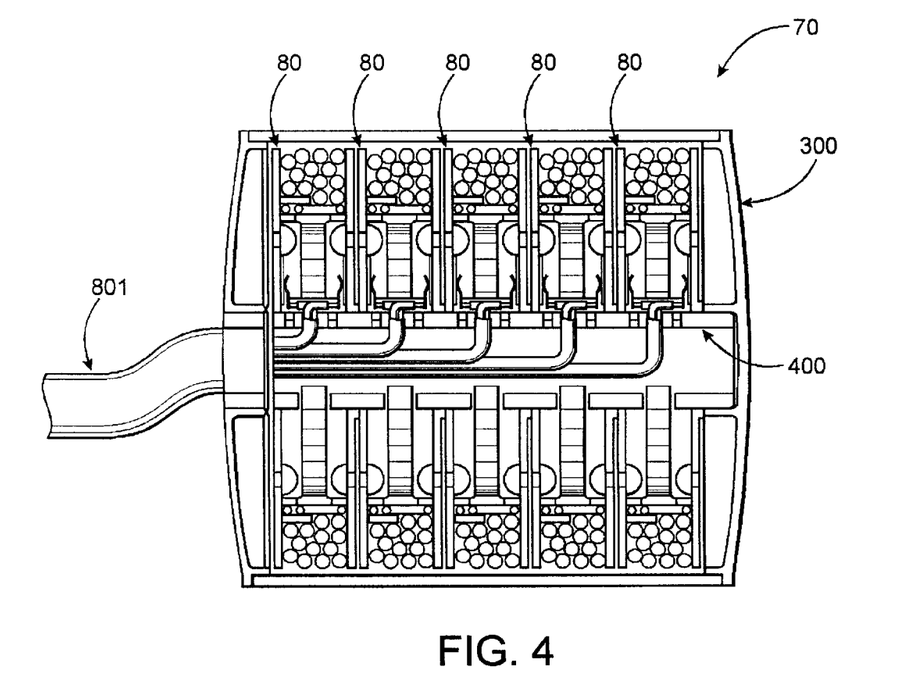
FIG. 4 is a longitudinal section of the leadwire assembly of the present invention including multiple retractor units of the first embodiment.
Figure 4A:
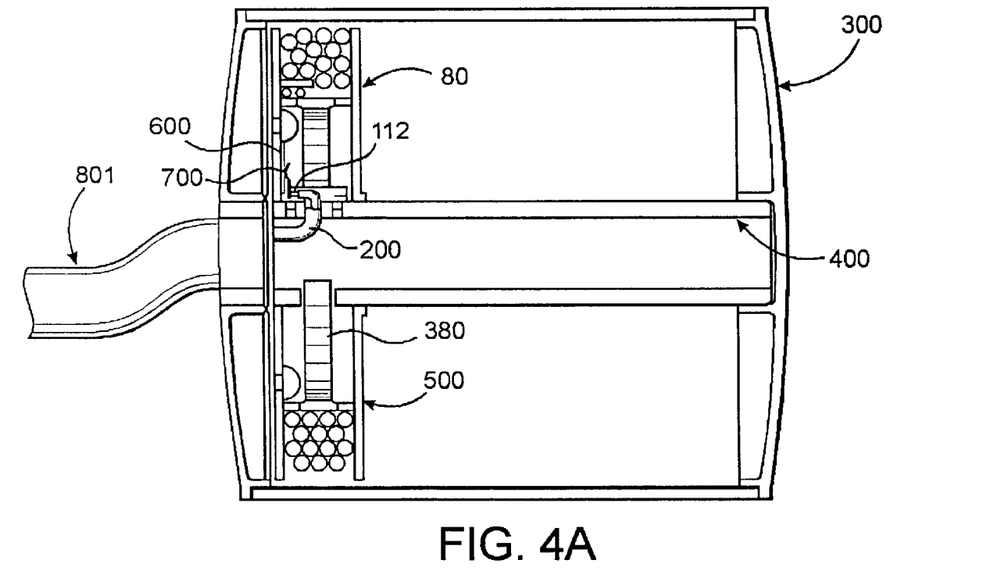
FIG. 4A is a longitudinal section of another embodiment of one retractor unit of the leadwire assembly of the present invention including one component wire within the leadwire.
Figure 4B:
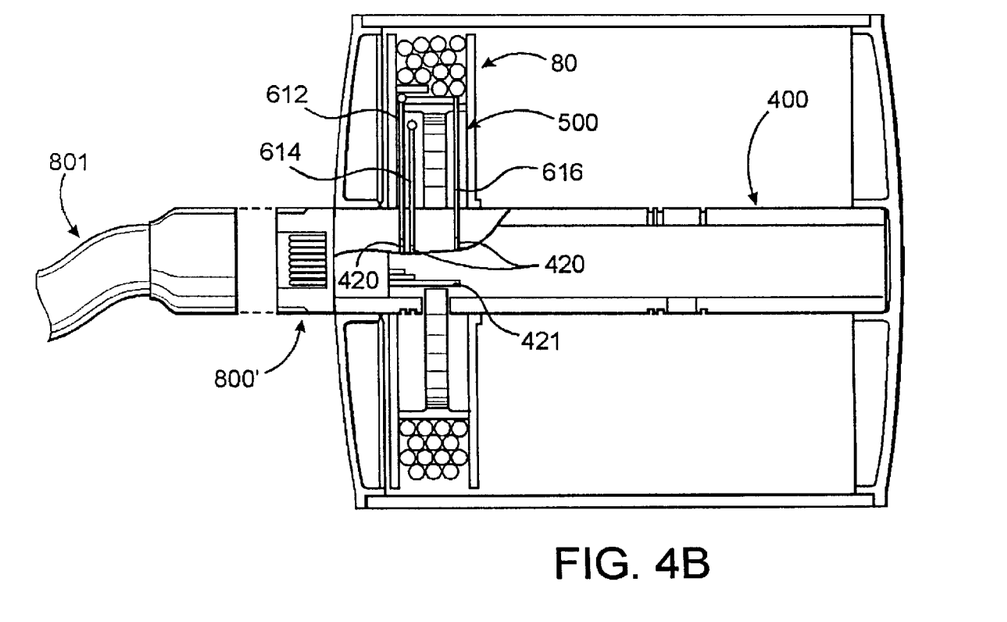
FIG. 4B is a longitudinal section of yet another alternative embodiment of one retractor unit of the leadwire assembly of the present invention including three component wires within the leadwire.

FIG. 4B illustrates yet another embodiment of the present invention, which is preferably implemented when more than two component wires are included in the anterior leadwire 100'. In this embodiment, each preferably individually insulated component wire is conductively affixed at its proximal end to an elongate, electrically conductive finger 612, 614, and 616 that extends from the reel 500 onto the shaft 400. In this embodiment, however, the shaft 400 includes a plurality of external circumferential grooves 420. Each of the flexible fingers 612, 614, 616 is aligned with its corresponding groove 420, and its natural spring action biases it against the base of the groove 420. Each of the fingers 612, 614, 616 rides within its groove 420 as the reel 500 rotates about the shaft 400 to unwind the anterior leadwire 100'. The base of each groove 420 is coated with a conductive material, so that the current travels from the finger contacts 612, 614, 616 to the conductive coating in the base of the external groove 420, through an aperture in the shaft 400 located at the bottom of the groove 420, the interior of which is also coated. In this way, each electrical signal travels from the base of the external groove 420, through the wall of the shaft 400, and preferably down a longitudinally disposed conductively coated strip 421 on the inside of the shaft 400. A housing connector 800' mates with the end of the shaft 400 in such a way that each electrical signal is transmitted from its longitudinal strip 421 on the inside of the shaft 400 to a corresponding contact on the housing connector 800'. Each signal is then transmitted along a preferably individually insulated medial leadwire within a common cable 801 to its corresponding port on the receiving means. This electrical connection preferably includes a pin connector type configuration 800. Note that this embodiment may also be used with an anterior leadwire 100' that includes only one or two component wires.

Figure 2:
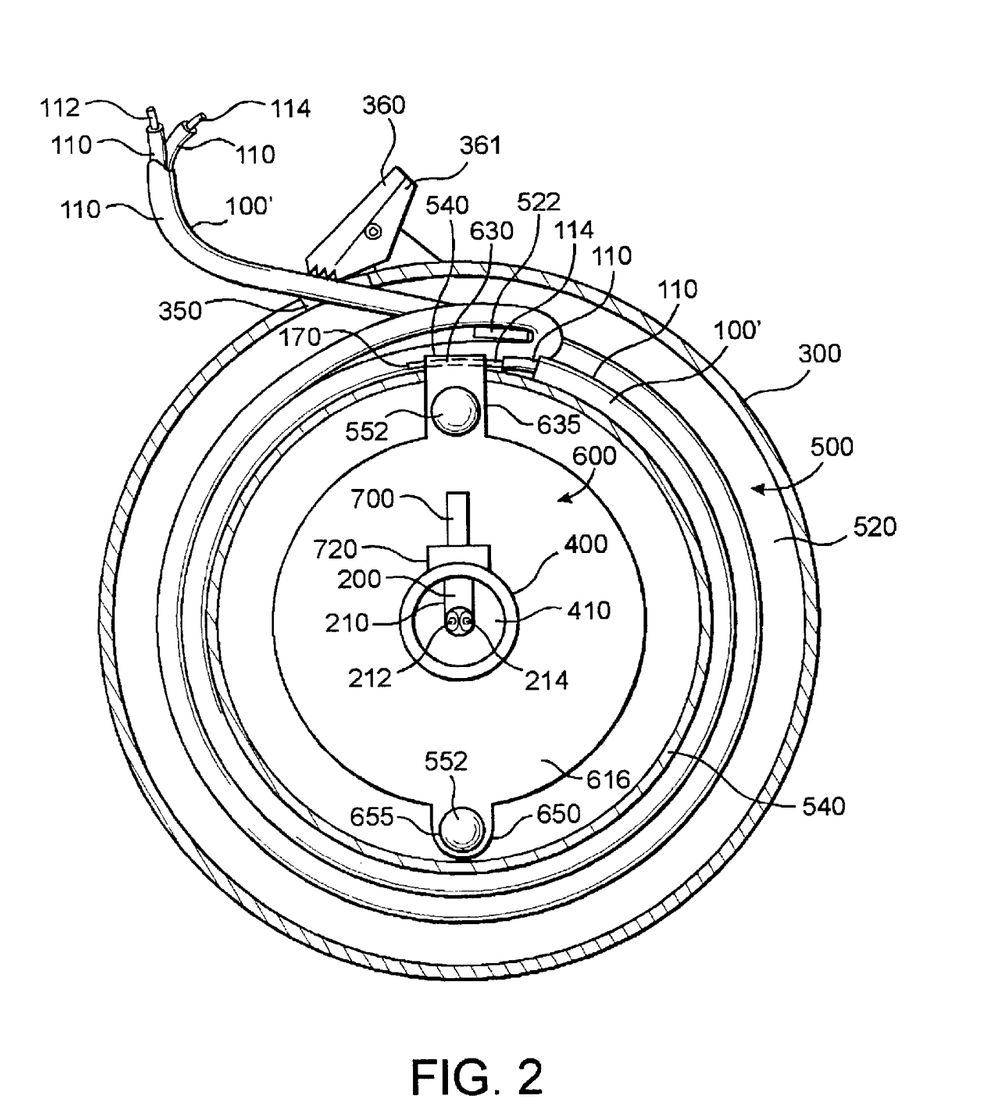
FIG. 2 is a cross-section of the first embodiment of one retractor unit of the leadwire assembly of the present invention along line 2—2 of FIG. 1.

FIG. 2 illustrates a cross-section of the first embodiment of the present invention, taken along line 2—2 in FIG. 1, which better illustrates some features not included in FIG. 1. Namely, FIG. 2 shows more clearly the function of anterior anchor post 522. The anterior leadwire 100' is reverse wrapped, first in a clockwise fashion (in this figure) around drum 540, and then turned around anchor post 522 so that it then wraps around drum 540 in a counterclockwise fashion. This configuration functions to reduce the tension placed on the connection of the anterior leadwire 100' to the anterior contact 600. Of course, such an anchor post is not required if the pin 660 and 661 connector of FIGS. 6A and 6B is utilized.

FIG. 2 also illustrates the main housing 300 which encases reel 500. Preferably, the anterior leadwire 100' passes through housing 300 at exit port 350. Additionally, FIG. 2 illustrates one embodiment of the locking mechanism (generally referred to as a "retraction gate"). Specifically, the locking mechanism is structured and disposed to prevent the anterior leadwire 100' from retracting from a desired extended position due to the torsion on the reel 500 exerted by the spring 380 (not shown in FIG. 2). In this embodiment, a cleat-lock apparatus 360, preferably in the form of a spring-loaded clamp, is included as the locking mechanism, although a cam or alternative locking mechanism could be incorporated. The cleat-lock 360 is spring-loaded by a torsion spring 361 into the closed position shown, preventing the anterior leadwire 100' from retracting into the unit. In particular, tension from the spring 380 causes the cleat-lock 360 to dig into the insulation 110 of the anterior leadwire 100'. Further, the cleat-lock 360 preferably includes at least one tooth-like ridge structured to engage the anterior leadwire 100', but not damage the insulation 110, and is formed of a material that will resist wear, such as steel or anodized aluminum. Additionally, the cleat-lock 360 is structured such that if the anterior leadwire 100' is pulled from the unit, the tension exerted by the spring of the cleat-lock 360 will be overcome and the cleat-lock 360 will therefore not impede outward motion of the anterior leadwire 100. In order to retract the anterior leadwire 100', the cleat-lock 360 is pressed into its open position so that its teeth do not engage the insulation 110. As such, the tension from spring 380 is able to freely retract the anterior leadwire 100' without opposition. Although not illustrated here, the cleat-lock 360 could be constructed flush with the housing 300 to reduce the chance that it will be accidentally depressed. Alternatively, or in addition to the above, a sliding protective shield could provide for and/or enhance the same function.

Figure 3:
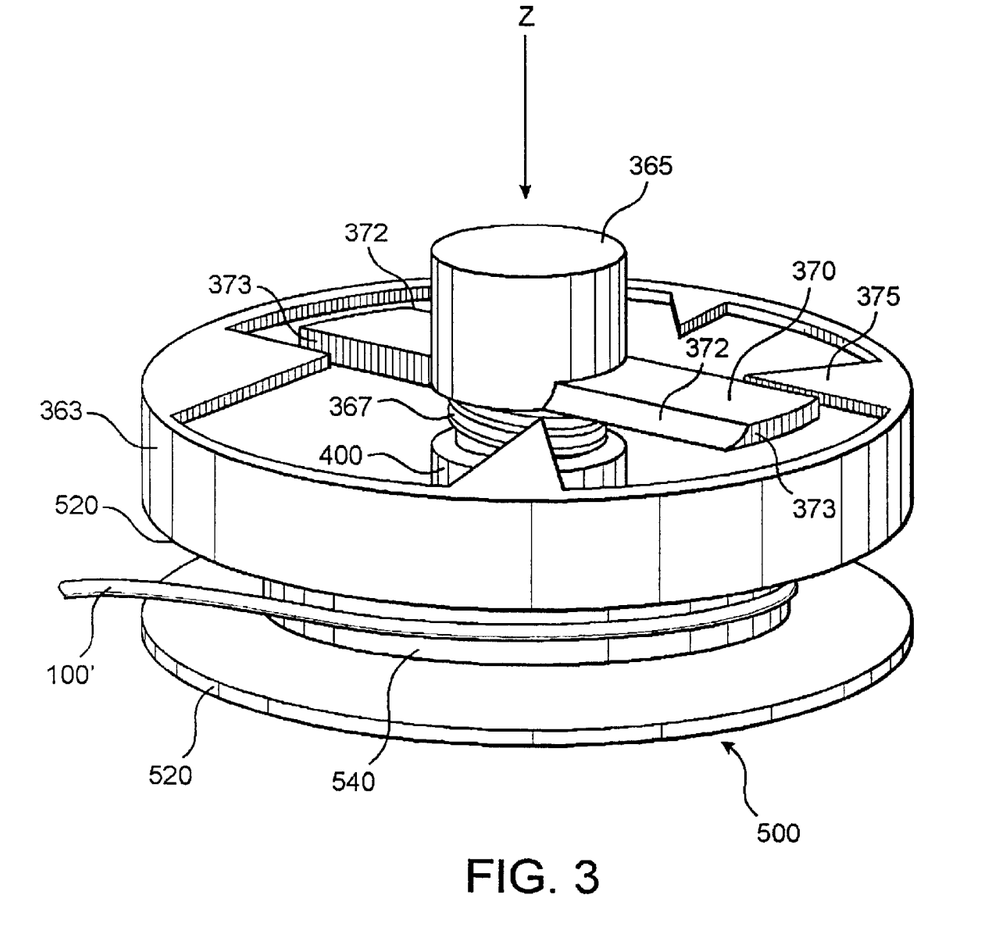
FIG. 3 is an isometric view of another embodiment of one retractor unit of the leadwire assembly of the present invention illustrating an alternative embodiment of the retraction gate.

It is also seen that various alternative mechanisms can serve the function of retraction gate. For example, a pawl-and-ratchet mechanism or a cam mechanism, as illustrated in FIG. 3, can be employed. In this embodiment, the basic reel 500 is shown with drum 540 and flanges 520. Additionally, however, a rim 363 extends from the exterior of one of the flanges 520. Further, corresponding stop wedges 375 extend inward from the rim 363 and a button 365 is spring-mounted to the shaft 400 and keyed so that it will not rotate. Blades 370 extend outward from the button 365 such that they engage the stop wedges 375. Preferably, each of the blades 370 include a tapered leading edge 372 and a flat trailing edge 373. In use, anterior leadwire 100' is retracted (wrapped around drum 540) as reel 500 is rotated counter clockwise (if viewing the unit from above) under the biasing of spring 380 (not shown in FIG. 3) which tends to force the reel 500 in that direction. However, if the button 365 is not depressed (compressing button spring 367), the stop wedges 375 will engage the flat trailing edges 373 of the blades 370, preventing further rotation. Accordingly, depressing button 365 allows the stop wedges 375 to clear the flat trailing edges 373, which in turn permits the reel 500 to rotate in the retracting direction. Conversely, if anterior leadwire 100' is extended, causing the reel 500 to rotate clockwise, the stop wedges 375 will encounter the tapered leading edges 372 of the blades 370. As the stop wedges 375 and leading edges 372 press together, blades 370 will be displaced in the direction indicated by the arrow Z, compressing spring 367 and allowing the blades 370 to slide past the stop wedges 375.

A preferred embodiment of the present invention will include multiple, and preferably 5 or 10, retractor units 80 within the leadwire assembly 70. Although each retractor unit may be configured to stand alone within an individual housing, it is preferred that all, or at least some, of the retractor units 80 be contained within a single main housing 300. Turning to FIGS. 4, 5, 5A & 5B, various arrangements of multiple retractor units shall be discussed. With regard to the mechanism chosen to serve the function of retraction gate, this will be driven in large part by the manner in which the multiple reels are juxtaposed. For example, the mechanism illustrated in FIG. 3 would not be well suited to an end-to-end arrangement in which the multiple reels share a common shaft, but may be better suited for a side-by-side arrangement. This will be clearer later, as the various arrangements are discussed. It can also be noted that, in theory, a locking mechanism is not necessary and the reels can be wound and unwound by hand. Such a configuration, however, will substantially increase the amount of work required to operate the leadwire assembly 70 of the electrocardiograph device 10.

FIG. 4 illustrates an embodiment of the present invention including multiple retractor units 80. The desired number of reels 500 (five shown here) are arranged end-to-end, sharing a common shaft 400. This design is simplest and requires the fewest parts, and it can be seen that 3 or 10 reels can also be arranged in this configuration, without any change in operation. Preferably, the main housing 300, which preferably incorporates a multi-part construction so as to facilitate access to an interior thereof for repairs and wire or reel changes, encloses all five reels 500 and is cylindrical in shape. Accordingly, shaft 400 must be somewhat elongate and have a large enough bore 410 to contain medial leadwires 200 from each of the reels 500. The entire device can be quite compact, less than four inches in length and diameter for a five leadwire assembly.

Further, as previously mentioned, all of the medial leadwires 200 are preferably joined via a common cable 801 to a standard ECG connector 800, its configuration dictated by the number of leadwires and the specific type of electrocardiograph monitoring unit. The leadwire assembly 70 can be adapted for use on most existing electrocardiograph monitoring units, which are commonly available; if the electrocardiograph monitoring unit and the connector 800 are not presently compatible, a standard adapter can be provided to allow connection. It is therefore seen that the leadwire assembly 70 may be independently available and provided for use to "retro-fit" existing units.

Returning to the embodiment of FIG. 4, although cylindrical, the base of the housing is preferably flat to allow the device to stand on a horizontal surface. A clip can also be provided, either incorporated into the base or added at the junction between the main housing and the common cable, to allow the device to be clamped to a cart, sheet, mattress, pillow, or the like, in order to prevent its inadvertent movement or possible disconnection from the patient, particularly when being moved. A magnetic or hook-and-loop backing may also be provided to facilitate storage of the assembly, both in and out of use.

Figure 5:
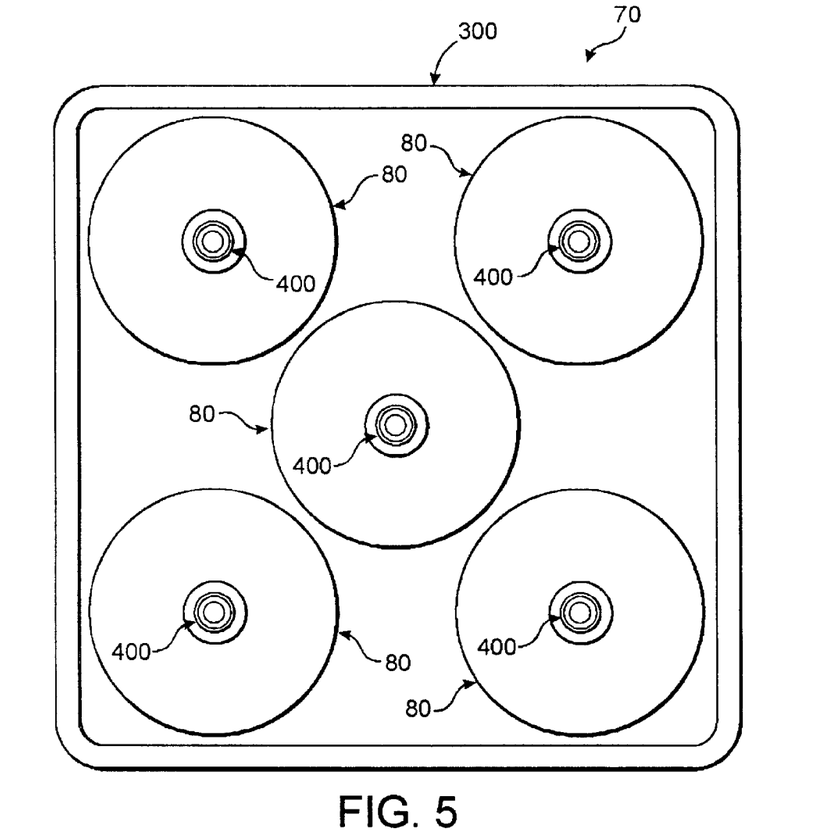
FIG. 5 is a plan view, with the housing cut away, of an embodiment of the leadwire assembly of the present invention including five multiple retractor units.
Figure 5A:
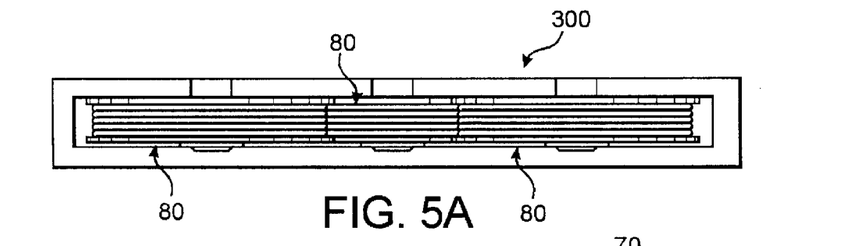
FIG. 5A is a cross-section of the embodiment of FIG. 5 including five retractor units.
Figure 5B:
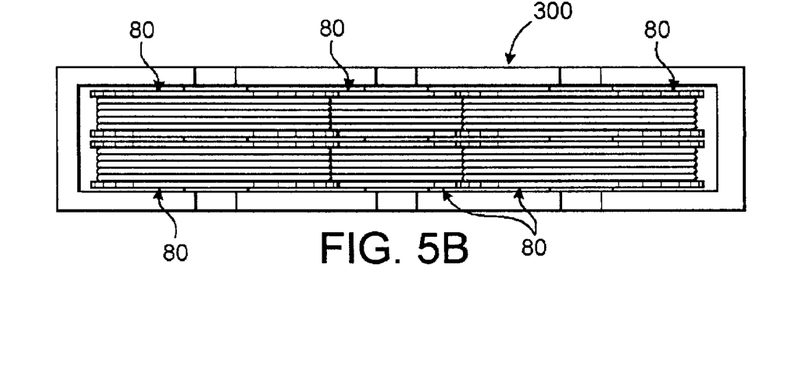
FIG. 5B is a cross-section of the embodiment of FIG. 5 including ten retractor units.

FIGS. 5 and 5A illustrate another embodiment which is more complicated but may be better suited for some applications. In this embodiment, the reels 500 of the individual retractor units 80 are arranged side-by-side, each having its own shaft 400. After the individual, preferably insulated, medial leadwires 200 exit their respective shafts 400, they then exit the housing 300, to travel within a common cable to the electrocardiograph monitoring unit. Each anterior leadwire 100 exits the housing 300 through its own exit port (see FIG. 1A). In this embodiment, the housing 300 will be flat on all sides and relatively slim. This can be important in operating rooms where space is limited and table or patient position is not always horizontal, because it can be tucked under the pillow or mattress pad. The housing will also preferably incorporate a multi-part construction so as to facilitate access to an interior thereof for repairs and wire or reel change. Again, an exterior clip or fastener may be provided. While the embodiment shown is a "five-leadwire" (5 reel) configuration, additional retractor units 80 may be added or removed. In the "fiveleadwire" configuration, the main housing can be less than eight inches on each side and less than one-and-a-half inches thick. Also, ten reels 500 can be arranged in this manner simply by stacking an additional five reels directly on top of the reels 500 shown. This results in the combination end-to-end/side-to-side configuration shown in FIG. 5B, which can still be less than two inches thick. A protective shield covering the, preferably push button/cam, release mechanisms is recommended for all configurations.

It should be noted that in any configuration, it is possible that not all the leadwires need be retractable, even though such a configuration is not preferred. Specifically, the precordial leadwires are generally shorter than the limb leadwires and therefore may be of standard non-retractable wires. This will allow the invention to be built with fewer reels, which will reduce the size and weight of the device. In this configuration, the precordial leadwires can be maintained somewhat untangled by use of a spacer bar placed between the leadwires. Moreover, although it is generally preferred to provide all wires with individual insulation, in some instances, depending upon the function performed by a particular wire, the insulation may not be necessary and can be effectively omitted.

While this invention has been shown and described in what are considered to be practical and preferred embodiments, it is recognized that departures may be made within the spirit and scope of this invention which should, therefore, not be limited except as set forth in the claims which follow and within the doctrine of equivalents.

What is claimed is:

1. An electrode cardiograph leadwire assembly structured to electrically communicate information between a monitor and a plurality of electrodes securable to a patient's skin, said electrode cardiograph leadwire assembly comprising:

a plurality of leadwires each interconnected in electrical communication between a different one of the electrodes and the monitoring unit and structured to provide transmission of cardiac electrical signals received by the plurality of electrodes, a main housing structured and disposed to contain at least one of said leadwires in individual isolated, retracted relation therein; and retraction means for selectively retracting said at least one leadwire into said main housing such that a portion of said at least one leadwire that is exposed from said housing can be individually controlled, and such that said at least one leadwire is maintained substantially untangled and prepared for extension from said main housing.

2. An electrocardiograph leadwire assembly as recited in claim 1 wherein said retraction means of said leadwire assembly further comprises:

at least one shaft;

at least one anterior contact rotatably disposed about said shaft;

at least one medial contact, said medial contact including a contact end and a medial end;

said medial end of said medial contact being secured to said shaft;

said contact end of said medial contact being disposed in conductive abutment with said anterior contact such that upon said anterior contact rotating about said shaft, said anterior contact also rotates relative to said contact end of said medial contact while maintaining conductive abutment therewith;

an anterior leadwire included as part of said at least one leadwire, said anterior leadwire including a proximal end and a distal end;

said distal end of said anterior leadwire being structured and disposed for conductive engagement with at least one of said electrodes, so as to receive said electrical signal from said patient's heart which is received by said electrode connected therewith;

said proximal end of said anterior leadwire being conductively affixed to said anterior contact;

a medial leadwire, said medial leadwire including a proximal end and a distal end;

said distal end of said medial leadwire being conductively affixed to said medial contact, and said proximal end of said medial leadwire being structured and disposed for conductive engagement with said associated port on said receiving means so as to transmit said electrical signal received by said electrode thereto; and said anterior leadwire including a retracted orientation and an extended orientation, said retracted orientation including a substantial part of said anterior leadwire wound generally about said shaft and contained within said housing, and said extended orientation including a portion of said anterior leadwire extended from said housing into connecting relation with said electrode on the patient's body.

3. An electrocardiograph leadwire assembly as recited in claim 2 wherein said anterior leadwire is structured to wind around said shaft into said retracted orientation upon rotation of said anterior contact in a first direction about said shaft, and said anterior leadwire is structured to unwind from said shaft into said extended orientation upon rotation of said anterior contact in a second direction about said shaft, opposite said first direction.

4. An electrocardiograph leadwire assembly as recited in claim 3 wherein said retraction means of said leadwire assembly further includes biasing means structured and disposed to bias said anterior contact to rotate about said shaft in said first direction.

5. An electrocardiograph leadwire assembly as recited in claim 4 wherein retraction means of said leadwire assembly further includes retraction gate means structured and disposed to selectively oppose rotation of said anterior contact in said first direction.

6. An electrocardiograph leadwire assembly as recited in claim 5 wherein said shaft of said retraction means of said leadwire assembly is generally hollow and includes at least one open end and an aperture in an exterior sidewall thereof, said medial leadwire being structured and disposed to extend through said aperture, into said shaft and then out of said open end of said shaft for engagement with said associated port on said receiving means of the electrocardiograph monitoring unit.

7. An electrocardiograph leadwire assembly as recited in claim 6 wherein said retraction means of said leadwire assembly further includes a reel rotatably fixed about said shaft, said reel comprising a cylindrical drum disposed in spaced, concentric relation about said shaft and at least one flange, said cylindrical drum being structured and disposed to receive said anterior leadwire in wound, wrapped relation thereabout.

8. An electrocardiograph leadwire assembly as recited in claim 7 wherein said drum of said reel of said leadwire assembly further includes an aperture formed therein and structured to permit conductive engagement between said proximal end of said anterior leadwire and said anterior contact.

9. An electrocardiograph leadwire assembly as recited in claim 8 wherein said anterior contact of said leadwire assembly is generally ring-shaped and is secured to said flange of said reel between said shaft and said drum of said reel such that said anterior contact may rotate directly about said shaft.

10. An electrocardiograph leadwire assembly as recited in claim 9 wherein said anterior contact of said leadwire assembly includes a contact appendage extending from said anterior contact through said aperture in said drum of said reel into conductive engagement with said proximal end of said anterior leadwire.

11. An electrocardiograph leadwire assembly as recited in claim 10 wherein said main housing of said leadwire assembly includes at least one exit port and is secured to said shaft of said retraction means about said reel, said anterior leadwire being structured to pass through said exit port for engagement at said distal end of said anterior leadwire with said electrode for receiving said cardiac electrical signal.

12. An electrocardiograph leadwire assembly as recited in claim 11 wherein said retraction gate means comprises a locking mechanism affixed to said housing for selectively limiting the movement of said anterior leadwire.

13. An electrocardiograph leadwire assembly as recited in claim 12 wherein said main housing of said leadwire assembly is structured to contain said plurality of leadwires, each of said leadwires being structured and disposed for individual, isolated, retracted containment therein.

14. An electrocardiograph leadwire assembly as recited in claim 13 wherein each of said plurality of leadwires includes one of said retraction means contained within said main housing.

15. An electrocardiograph leadwire assembly as recited in claim 2 wherein said anterior leadwire includes at least one conductive wire therein extending from said distal end to said proximal end of said anterior leadwire, and said retraction means includes at least one of said anterior contacts, said one of said anterior contacts being connected to a corresponding one of said conductive wires of said anterior leadwire.

16. An electrocardiograph leadwire assembly as recited in claim 15 wherein said medial leadwire includes at least one conductive wire extending from said distal end to said proximal end of said medial leadwire, and said retraction means includes at least one of said medial contacts, said one of said medial contacts being connected to a corresponding one of said conductive wires of said medial leadwire.

17. An electrode cardiograph leadwire assembly structured to electrically communicate information between a monitor unit and a plurality of electrodes securable to a patients skin, said electrode cardiograph leadwire assembly comprising:

a plurality of leadwires each interconnected in electrical communication between a different one of the electrodes and the monitoring unit and structured to provide transmission of cardiac electrical signals received by the plurality of electrodes, a main housing structured and disposed to contain at least one of said leadwires in individual, isolated, retracted relation therein;

retraction means included in said main housing for collectively retracting said at least one leadwire into said main housing such that a portion thereof that is exposed from said housing can be individually controlled, and such that said at least one leadwire is maintained substantially untangled and prepared for extension from said main housing; and coupling means structured for interconnecting said plurality of leadwires in information transmitting communication with the monitoring unit.

18. An electrocardiograph leadwire assembly as recited in claim 17 wherein said retraction means further comprise:

at least one shaft;

at least one anterior contact rotatably disposed about said shaft;

at least one medial contact, said medial contact including a contact end and a medial end;

said medial end of said medial contact being secured to said shaft;

said contact end of said medial contact being disposed in conductive abutment with said anterior contact such that upon said anterior contact rotating about said shaft, said anterior contact also rotates relative to said contact end of said medial contact while maintaining conductive abutment therewith;

an anterior leadwire included as part of said at least one leadwire, said anterior leadwire including a proximal end and a distal end;

said distal end of said anterior leadwire being structured and disposed for conductive engagement with one of said electrodes, so as to receive said electrical signal from said patient's heart which is received by said electrode connected therewith;

said proximal end of said anterior leadwire being conductively affixed to said anterior contact; and a medial leadwire, said medial leadwire including a proximal end and a distal end;

said distal end of said medial leadwire being conductively affixed to said medial contact, and said proximal end of said medial leadwire being structured and disposed for conductive engagement with said associated port on said receiving means through said coupling means so as to transmit said electrical signal received by said electrode thereto; and said anterior leadwire including a retracted orientation and an extended orientation, said retracted orientation including a substantial part of said anterior leadwire wound generally about said shaft and contained within said housing, and said extended orientation including a portion of said anterior leadwire extended from said housing into connecting relation with the electrode on the patient's body.

19. An electrocardiograph leadwire assembly as recited in claim 18 wherein said anterior leadwire is structured to wind around said shaft into said retracted orientation upon rotation of said anterior contact in a first direction about said shaft, and said anterior leadwire is structured to unwind from said shaft into said extended orientation upon rotation of said anterior contact in a second direction about said shaft, opposite said first direction, and said retraction means further include biasing means structured and disposed to bias said anterior contact to rotate about said shaft in said first direction.

20. An electrocardiograph leadwire assembly as recited in claim 19 wherein said retraction means further include a reel rotatably fixed about said shaft, said reel comprising a cylindrical drum disposed in spaced, concentric relation about said shaft and at least one flange, said cylindrical drum being structured and disposed to receive said anterior leadwire in wound, wrapped relation thereabout.

21. An electrocardiograph leadwire assembly as recited in claim 20 wherein said main housing is structured to contain said plurality of leadwires, each of said leadwires being structured and disposed for individual, isolated, retracted containment therein, and each of said plurality of leadwires including one of said retraction means contained within said main housing.

22. An electrode cardiograph leadwire assembly structured to electrically communicate information between a monitor and a plurality of electrodes securable to a patient's skin, said electrode cardiograph leadwire assembly comprising:

a plurality of leadwires each interconnected in electrical communication between a different one of the electrodes and the monitoring unit and structures to provide transmission of cardiac electrical signals received by the plurality of electrodes, a main housing structured and disposed to contain at least one of said leadwires in individual isolated, retracted relation therein; and retraction means for selectively retracting said at least one leadwire into said main housing such that a portion of said at least one leadwire that is exposed from said housing can be individually controlled, and such that said at least one leadwire is maintained substantially untangled and prepared for extension from said main housing;

at least one shaft; at least one groove disposed about a perimeter of said shaft; a conductive material coating disposed within said groove; and at least one elongate, electrically conductive finger, said conductive finger being structured and disposed to ride in said groove, in conductive abutment with said conductive material such that upon said conductive finger rotating about said shaft, said conductive finger maintains conductive abutment within said groove.

23. An electrical cardiograph leadwire assembly as recited in claim 22 further comprising said at least one leadwire including an interior leadwire, said interior leadwire including a proximal end and a distal end; said distal end of said interior leadwire being structured and disposed for conductive engagement with at least one of the electrodes so as to receive electrical signals from the patient, said proximal end of said interior leadwire being conductively affixed to said conductive finger; said conductive material coating being electrically interconnected to the monitoring unit through said coupling means so as to transmit electrical signals received from the electrodes.

24. An electrode cardiograph leadwire assembly as recited in claim 23 further comprising said interior leadwire including a retracted orientation and an extended orientation, said retracted orientation including a substantial part of said interior leadwire wound generally about said shaft and contained within said housing, said extended orientation including a portion of said interior leadwire extended from said housing into connecting relation with the electrode on the patient's skin.

25. An electrode cardiograph leadwire assembly structured to electrically communicate information between a monitor unit and a plurality of electrodes securable to a patient's skin, said electrode cardiograph leadwire assembly comprising:

a plurality of leadwires each interconnected in electrical communication between a different one of the electrodes and the monitoring unit and structured to provide transmission of cardiac electrical signals received by the plurality of electrodes, a main housing structured and disposed to contain at least one of said leadwires in individual, isolated, retracted relation therein;

retraction means included in said main housing for collectively retracting said at least one leadwire into said main housing such that a portion thereof that is exposed from said housing can be individually controlled, and such that said at least one leadwire is maintained substantially untangled and prepared for extension from said main housing; and coupling means structured for interconnecting said plurality of leadwires in information transmitting communication with the monitoring unit;

at least one shaft; at least one groove disposed about a perimeter of said shaft; a conductive material coating disposed within said groove, at least one elongate, electrically conductive finger, said conductive finger being structured and disposed to ride in said groove, said conductive finger being disposed in conductive abutment with said conductive material such that upon rotation of said conductive finger about said shaft, said conductive finger maintains conductive abutment within said groove.

26. An electrode cardiograph leadwire assembly as recited in claim 25 further comprising an interior leadwire as part of said at least one leadwire, said interior leadwire including a proximal end and a distal end; said distal end of said interior leadwire being structured and disposed for conductive engagement within one of said electrodes, so as to receive an electrical signal from the electrode connected to said one leadwire and the patient's skin, said proximal end of said interior leadwire being conductively affixed to said conductive finger.

27. An electrode cardiograph leadwire assembly as recited in claim 26 wherein said conductive material coating is electrically and conductively interconnected to said coupling means, said interior leadwire including a retracted orientation and an extended orientation, said retracted orientation including a substantial part of said interior leadwire wound generally about said shaft and contained within said housing, and said extended orientation including a portion of said interior leadwire from said housing into connecting relation with the electrode on the patient's skin.

* * * * *